United States Patent
Kim et al.

(10) Patent No.: US 6,932,964 B1
(45) Date of Patent: Aug. 23, 2005

(54) COSMETIC COMPOSITION WITH WATER-SOLUBLE OR WATER-DISPERSIBLE POLYMERS

(75) Inventors: Son Nguyen Kim, Hemsbach (DE); Axel Sanner, Frankenthal (DE); Peter Hössel, Schifferstadt (DE); Wilma M. Dausch, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/382,708

(22) Filed: Aug. 24, 1999

(30) Foreign Application Priority Data

Aug. 26, 1998 (DE) .......................................... 198 38 851

(51) Int. Cl.$^7$ ............................ A61K 7/06; A61K 9/00
(52) U.S. Cl. ................ 424/70.16; 424/70.1; 424/70.11; 424/70.12; 424/70.15; 424/43
(58) Field of Search ............................ 424/70.16, 70.1, 424/70.11, 70.12, 70.15, 43, 401, 47

(56) References Cited

U.S. PATENT DOCUMENTS

| | | | |
|---|---|---|---|
| 3,836,537 A | | 9/1974 | Boerwinkle et al. .......... 260/29 |
| 4,237,253 A | | 12/1980 | Jacquet et al. ................. 526/75 |
| 4,324,780 A | | 4/1982 | Jacquet et al. ................. 424/47 |
| 4,717,739 A | * | 1/1988 | Chevreux et al. ............. 156/99 |
| 4,748,989 A | * | 6/1988 | Nuber et al. .................... 132/7 |
| 4,767,613 A | * | 8/1988 | Nuber et al. .................. 424/47 |
| 4,800,220 A | * | 1/1989 | Ribba .................... 526/538.23 |
| 4,814,101 A | | 3/1989 | Schieferstein et al. ...... 252/174 |
| 5,196,188 A | | 3/1993 | Potthoff-Karl et al. ........ 424/71 |
| 5,278,269 A | * | 1/1994 | Mita et al. ................ 526/303.1 |
| 5,306,484 A | | 4/1994 | Potthoff-Karl et al. ........ 424/47 |
| 5,344,643 A | | 9/1994 | Thiel et al. ..................... 424/70 |
| 5,632,998 A | * | 5/1997 | Midha et al. ................. 424/401 |
| 5,635,169 A | * | 6/1997 | Blankenburg et al. ... 424/70.15 |
| 6,132,707 A | | 10/2000 | Dubief et al. ............. 424/78.08 |
| 6,140,435 A | * | 10/2000 | Zanotti-Russo ............. 524/916 |
| 6,630,136 B1 | | 10/2003 | Dubief et al. ............. 424/78.08 |

FOREIGN PATENT DOCUMENTS

| | | |
|---|---|---|
| CA | 2066226 | 3/1991 |
| CA | 2148805 | 6/1994 |
| DE | 4225045 | 7/1992 |
| DE | 4314305 | 4/1994 |
| EP | 100890 | 2/1984 |
| EP | 257444 | 3/1988 |
| EP | 372546 | 6/1990 |
| EP | 379082 | 7/1990 |
| EP | 728778 | 8/1996 |
| JP | 5750912 | 9/1980 |
| JP | 1213221 | 2/1988 |
| JP | 3206023 | 12/1989 |
| JP | 3206024 | 12/1989 |
| WO | 97/00664 | 1/1997 |
| WO | WO 97/12586 | 4/1997 |
| WO | 98/00096 | 1/1998 |

OTHER PUBLICATIONS

Derwent abstract 94–043715/06, (1994).*

Derwent abstract 91–307303/42, (1991).*

Derwent abstract 91–307304/42, (1991).*

Derwent abstract 35999 E/18, (1982).*

Derwent abstract 94–342756/43, (1994).*

Derwent abstract 89–289741/40, (1989).*

Fikentscher, *Cell. Chem.*, 13, 1932, 58–64, 71, 74.

* cited by examiner

*Primary Examiner*—Shengjun Wang
(74) *Attorney, Agent, or Firm*—Novak Druce & Quigg

(57) ABSTRACT

A cosmetic composition comprising at least one water-soluble or water-dispersible polymer which comprises, in copolymerized form, a) at least one α,β-ethylenically unsaturated monomer of the formula I

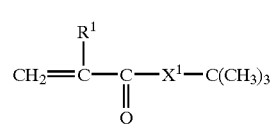

(I)

in which
R$^1$ is hydrogen or C$_1$–C$_8$-alkyl, and
X$_1$ is O or NR$^2$, where R$^2$ is hydrogen, C$_1$–C$_8$-alkyl or if C$_5$–C$_8$-cycloalkyl, b) at least one α,β-ethylenically unsaturated mono- and/or dicarboxylic acid, c) at least one compound having at least one α,α-ethylenically unsaturated double bond and at least 5 alkylene oxide units per molecule, d) at least one compound having at least one α,β-ethylenically unsaturated double bond and at least one straight-chain or branched C$_8$–C$_{30}$-alkyl or -alkylene radical per molecule, where the components c) and/or d) can be partially or completely replaced by a component e), where e) is at least one compound having at least one α,β-ethylenically unsaturated double bond, at least 5 alkylene oxide units and at least one straight-chain or branched C$_8$–C$_{30}$-alkyl or -alkylene radical per molecule, or the salts thereof.

10 Claims, No Drawings

COSMETIC COMPOSITION WITH WATER-SOLUBLE OR WATER-DISPERSIBLE POLYMERS

This application claims foreign priority of Germany 1983751.9, filed Aug. 26, 1998. The present invention relates to a cosmetic composition which comprises, in copolymerized form, at least one water-soluble or water-dispersible polymer.

In cosmetics, polymers with film-forming properties are used for setting, improving structure and styling hair. These hair-treatment compositions generally comprise a solution of the film former in an alcohol or a mixture of alcohol and water.

Hair-setting compositions are generally sprayed onto the hair in the form of aqueous-alcoholic solutions. After the solvent has evaporated, the hair is held in the desired shape at the mutual points of contact by the polymer which remains. The polymers should firstly be hydrophilic so that they can be washed out of the hair, but secondly should be hydrophobic so that the hair treated with the polymers retains it shape even when atmospheric humidity is high and does not stick together. In order to achieve as efficient a hair-setting action as possible, it is furthermore desirable to use polymers which have a relatively high molecular weight and a relatively high glass transition temperature (at least 15° C.

Another current demand on hair-treatment compositions is that they should impart to the hair a natural appearance and shine even, for example, when the hair concerned is by its very nature particularly strong and/or dark.

A disadvantage of many known hair-setting polymers is the so-called "flaking" effect, i.e. after combing, a white, flaky residue remains on the hair. This is generally considered by users to be extremely unpleasant. The "flaking" effect is particularly evident in people with a dark hair color and/or particularly thick hair. The possibility of using hair-setting formulations which have this effect is thus considerably impaired in particular in the Asian market. Possible causes of the "flaking" effect are regarded inter alia as the chemical structure of the hair-setting polymers used and, in particular, the particle size of the spray. In addition to the above-mentioned properties, hair-setting polymers should therefore preferably have high propellant gas compatibility in order to permit formulation in spray cans under the highest possible pressure. This is true both for classical propellants based on propane/butane, and also for their replacements, e.g. those based on dimethyl ether.

EP-A-0 100 890, EP-A-0 257 444, DE-A-40 31 912 and DE A-39 01 325 describe copolymers which contain, in copolymerized form, at least one alkyl ester of acrylic acid or methacrylic acid, at least one N-vinyllactam, e.g. N-vinylpyrrolidone, and other monomers, and the use of these copolymers in hair-treatment compositions.

A disadvantage of the abovementioned N-vinylpyrrolidone-containing copolymers is that N-vinyllactams, such as N-vinylpyrrolidone, are readily reacted by acidic catalysis to give nonpolymerizable by-products, e.g. with ethanol to give 2-ethoxy-N-ethylpyrrolidone. These by-products are in reverse equilibrium with the free N-vinyllactam, meaning that products with a low molecular weight and a very high residual monomer content are usually obtained.

WO 97/00664 describes an aqueous nail polish which comprises an acrylic resin crosslinked with a difunctional urethane acrylate. The dried films are neither soluble in water nor dispersible in water, and because of their propane/butane incompatibility, are unsuitable for hair sprays.

EP-A-379 082 describes a hair-setting composition comprising, as film former, a copolymer which comprises, in copolymerized form,
A) from 75 to 99% by weight of tert-butyl (meth)acrylate,
B) from 1 to 25% by weight of (meth)acrylic acid and
C) from 0 to 10% by weight of another free-radically copolymerizable hydrophobic monomer.

Hair-setting compositions based on these copolymers which comprise only components A) and B) make the hair too hard and have too low a propane/butane compatibility. Copolymers which additionally comprise a monomer C) are in need of improvement as regards their ability to be washed off.

DE-A-43 14 305 describes, as does EP-A-379 082, a hair-setting polymer based on tert-butyl (meth)acrylate and (meth)acrylic acid which comprises, in copolymerized form, from 0 to 60% by weight of a $C_1$–$C_{18}$-alkyl (meth)acrylate or a mixture thereof with N—$C_1$–$C_{18}$-alkyl(meth) acrylamides. Although additional monomers with a carbon number of more than 8 in some circumstances lead to better propane/butane compatibility, the ability to be washed off is at the same time considerably impaired.

WO-A 98/00096 has a disclosure content which is similar to that of EP-A-379 082 and DE-A-4 314 305.

EP-A-0 372 546 and EP-A-0 728 778 describe film-former resins which comprise, in copolymerized form, at least one (meth)acrylamide, at least one $C_1$–$C_4$-alkyl (meth) acrylate, at least one N,N-dialkyl (meth)acrylate or N,N-dialkyl(meth)-acrylamide and optionally at least one hydroxyalkyl (meth)acrylate or polyalkylene glycol (meth) acrylate. Copolymers which comprise an α,β-ethylenically unsaturated mono- and/or dicarboxylic acid in copolymerized form are not described. These copolymers have only poor solubility in ethanol and the resulting films are hard, meaning that when they are used in hair-setting compositions, they do not impart a natural appearance to the hair. Their propane/butane compatibility is also in need of go improvement.

JP-A-57 050 912 describes a hair-treatment composition based on a nonionic hydrophilic oligoalkylene oxide (meth) acrylate having up to 10 alkylene oxide units, which makes the hair soft.

JP-A-03 206 023 describes a polymer resin for hair-treatment compositions which comprises, in copolymerized form,
a) from 6 to 35% by weight of acrylic acid, methacrylic acid, itaconic acid or a mixture thereof,
b) from 15 to 50% by weight of at least one $C_{10}$–$C_{18}$-alkyl (meth)acrylate,
c) from 15 to 50% by weight of at least one $C_4$–$C_8$-alkyl (meth)acrylate and
d) from 0 to 25% by weight of at least one other hydrophobic vinyl monomer.

The resulting copolymers are neutralized with a base. Like the hair-setting polymers described in EP-A-379 082 and DE-A-4 314 305, these copolymers too have a high proportion of hydrophobic monomers. Their ability to be washed off is therefore in need of improvement.

JP-A-03 206 024 describes a hair-setting polymer similar to that in JP-A-03 206 023 which additionally comprises, in copolymerized form, from 5 to 50% by weight of an N-alkyl-substituted acrylamide. The ability to be washed off of these polymers is also in need of improvement.

JP-A-01 213 221 describes a hair colorant comprising a tetrapolymer which comprises, in copolymerized form,
a) from 30 to 70% by weight of at least one (meth)acrylic ester of the formula

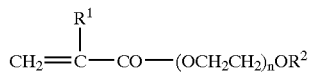

$R^1$ = H, CH$_3$; $R^2$ = CH$_3$, C$_2$H$_5$; n = 1–10 b) from 5 to 25% by weight of acrylic acid, methacrylic acid and/or itaconic acid,
c) from 5 to 20% by weight of at least one $C_8$–$C_{18}$-alkyl ester of acrylic acid and/or methacrylic acid,
d) from 20 to 50% by weight of at least one other vinyl monomer, chosen from n-butyl (meth)acrylate, isobutyl (meth)acrylate, cyclohexyl (meth)acrylate, vinyl acetate, vinylpyrrolidone, diaceto(meth)acrylamide, acrylonitrile or styrene,
and which is then neutralized with a water-soluble, organic base. Polymers which have a tert-butyl ester or an N-tert-butylamide of an α,β-ethylenically unsaturated carboxylic acid are not described. As a result of their high alkylene oxide content, these polymers form soft films and are therefore unsuitable as hair-setting compositions. In addition, their LPG compatibility is in need of improvement.

It is an object of the present invention to make available novel cosmetic compositions, in particular hair-treatment compositions which have high propellant gas compatibility and essentially do not show a "flaking" effect. Preferably, these compositions should impart smoothness and suppleness to the hair.

We have found that this object is achieved by cosmetic compositions which comprise at least one water-soluble or water-dispersible polymer which comprises, in copolymerized form, at least one tert-butyl ester and/or an N-tert-butylamide of an α,β-ethylenically unsaturated carboxylic acid, at least one α,β-ethylenically unsaturated mono- and/or dicarboxylic acid, at least one α,β-ethylenically unsaturated compound having at least 5 alkylene oxide units and at least one α,β-ethylenically unsaturated compound having a $C_8$–$C_{30}$-alkyl or -alkylene radical.

The present invention therefore relates to a cosmetic composition comprising at least one water-soluble or water-dispersible polymer which comprises, in copolymerized form,
a) at least one α,β-ethylenically unsaturated monomer of the

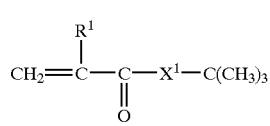

(I)

in which
$R^1$ is hydrogen or $C_1$–$C_8$-alkyl, and
$X^1$ is O or $NR^2$, where $R^2$ is hydrogen, $C_1$–$C_8$-alkyl or $C_5$–$C_8$-cycloalkyl, b) at least one α,β-ethylenically unsaturated mono- and/or dicarboxylic acid,
c) at least one compound having at least one α,β-ethylenically unsaturated double bond and at least 5 alkylene oxide units per molecule,
d) at least one compound having at least one α,β-ethylenically unsaturated double bond and at least one straight-chain or branched $C_8$–$C_{30}$-alkyl or -alkylene radical per molecule,
where the components c) and/or d) can be partially or completely replaced by a component e), where
e) is at least one compound having at least one α,β-ethylenically unsaturated double bond, at least 5 alkylene oxide units and at least one straight-chain or branched $C_8$–$C_{30}$-alkyl or -alkylene radical per molecule,
or the salts thereof.

The water-soluble or water-dispersible polymers used in the cosmetic compositions according to the invention can additionally comprise, in copolymerized form, up to 10% by weight, based on the total weight of the monomers to be polymerized, of at least one other free-radically copolymerizable monomer.

For the purposes of the present invention, the expression $C_1$–$C_8$-'alkyl' includes straight-chain and branched alkyl groups. They are preferably straight-chain or branched $C_1$–$C_6$-alkyl and particularly preferably $C_1$–$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

$C_8$–$C_{30}$-alkyl or $C_8$–$C_{30}$-alkylene are preferably straight-chain and branched alkyl or alkylene groups. Preference is given here to largely linear alkyl radicals, as occur in natural or synthetic fatty acids and fatty alcohols and also oxo alcohols, which optionally may be, additionally, mono- or di- or polyunsaturated. Examples thereof include n-hexyl (ene), n-heptyl(ene), n-octyl(ene), n-nonyl(ene), n-decyl (ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

The $C_5$-Ce-cycloalkyl group is, for example, cyclopentyl, cyclohexyl, cycloheptyl or cyclooctyl.

Component a)

Component a) is preferably an α,β-ethylenically unsaturated compound of the formula I, in which
$R^1$ is hydrogen, methyl or ethyl, and
$X^1$ is O or $NR^2$, where $R^2$ is hydrogen, methyl, ethyl, n-propyl, isopropyl, n-butyl, sec-butyl, tert-butyl or cyclohexyl.

It is also possible to use mixtures of compounds of component a).

Component a) is preferably tert-butyl acrylate, tert-butyl methacrylate, tert-butyl ethacrylate, N-tert-butylacrylamide, N-tert-butylmethacrylamide, N-tert-butylethacrylamide and mixtures thereof.

Component b)

Suitable α,β-ethylenically unsaturated mono- and dicarboxylic acids are, for example, acrylic acid, methacrylic acid, fumaric acid, maleic acid, itaconic acid, crotonic acid and mixtures thereof. Preference is given to using acrylic acid, methacrylic acid and mixtures thereof.

Componente c)

Component c) is preferably chosen from polyether acrylates of the formula II

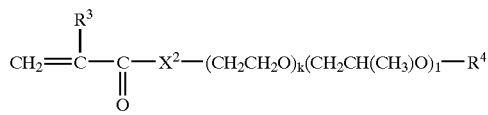

(II)

in which the order of the alkylene oxide units is arbitrary, k and 1 independently of one another are an integer from 0 to 50, the sum k+1 being at least 5, $R^3$ is hydrogen or $C_1$–$C_8$-alkyl, and $R^4$ is hydrogen or $C_1$–$C_6$-alkyl, $X^2$ is O or $NR^2$, where $R^2$ is hydrogen, $C_1$-Cg-alkyl or $C_5$–$C_8$-cycloalkyl.

The polyether acrylates c) are preferably compounds of the formula II in which the sum k+1 is an integer from 5 to 70, preferably from 6 to 50.

In formula II, $R^3$ is preferably hydrogen, methyl, ethyl, n-propyl, isopropyl, n-butyl, sec-butyl, tert-butyl, n-pentyl or n-hexyl, in particular hydrogen, methyl or ethyl.

$R^4$ in formula II is preferably hydrogen, methyl, ethyl, n-propyl, isopropyl, n-butyl, sec-butyl, n-pentyl or n-hexyl.

Preferably, $X^2$ in formula II is O or NH.

Suitable polyether acrylates c) are, for example, the polycondensation products of the abovementioned α,β-ethylenically unsaturated mono- and/or dicarboxylic acids and their acid chlorides, acid amides and anhydrides with polyetherols. Suitable polyetherols can be prepared easily by reacting ethylene oxide, 1,2-propylene oxide and/or epichlorohydrin with a starter molecule, such as water or a short-chain alcohol $R^4$—OH. The alkylene oxides can be used individually, alternately one after the other or as a mixture. The polyether acrylates c) can be used alone or in mixtures for the preparation of the polymers used according to the invention.

Component d)

Component d) is preferably chosen from compounds of the formula III

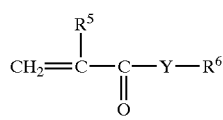

(III)

in which $R^5$ is hydrogen or Cl—Ce-alkyl, $R^6$ is a straight-chain or branched $C_8$–$C_{30}$-alkyl radical, and Y is O or $NR^7$, where $R^7$ is hydrogen, Cl-Ce-alkyl or $C_5$–$C_8$-cycloalkyl.

Preferably, in formula III, $R^5$ is hydrogen, methyl or ethyl. Y is preferably O or NH.

In particular, $R^6$ is n-octyl, ethylhexyl, 1,1,3,3-tetramethylbutyl, undecyl, lauryl, tridecyl, myristyl, pentadecyl, palmityl, margarinyl, stearyl, palmitoleinyl, oleyl or linolyl.

In particular, component d) is chosen from n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arachidyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate, n-octyl(meth) acrylamide, 1,1,3,3-tetramethylbutyl(meth)acrylamide, ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arachidyl(meth)acrylamide, behenyl(meth)acrylamide, lignocerenyl(meth)acrylamide, cerotinyl(meth)acrylamide, melissinyl(meth)acrylamide, palmitoleinyl(meth) acrylamide, oleyl(meth)acrylamide, linolyl(meth) acrylamide, linolenyl(meth)acrylamide, stearyl(meth) acrylamide, lauryl(meth)acrylamide and mixtures thereof.

Component e)

Component e) is preferably chosen from e1) polyether acrylates of the formula II, as defined above for component c), in which $R^4$ is $C_8$–$C_{30}$-alkyl, e2) urethane (meth)acrylates containing alkylene oxide groups, and mixtures thereof.

The polyether acrylates e1) are preferably compounds of the formula II in which the sum k+1 is an integer from 5 to 70, preferably from 6 to 50.

Preferably, for the polyether acrylates e1), $R^3$ has the preferred meanings given above for component c).

In the case of polyether acrylates e1) in formula II, $R^4$ is preferably n-octyl, ethylhexyl, 1,1,3,3-tetramethylbutyl, undecyl, lauryl, tridecyl, myristyl, pentadecyl, palmityl, margarinyl, stearyl, palmitoleinyl, oleyl or linolyl.

In the case of the polyether acrylates e1), in formula II, $X^2$ is preferably O or NH.

The preparation of the polyether acrylates e1) can, for example, be carried out in the same way as the preparation of c), i.e. by reacting an α,β-ethylenically unsaturated mono- and/or dicarboxylic acid, or a suitable derivative thereof, with a polyetherol, the starter molecules used for the preparation of these polyetherols being long-chain alcohols $R^4$—OH, in which $R^4$ is $C_8$–$C_{30}$-alkyl. The alkylene oxides can in turn be used individually, alternately one after the other or as a mixture for the preparation of the polyetherols. The polyether acrylates e1) can be used alone or in mixtures for the preparation of the polymers used according to the invention.

Preferred urethane (meth)acrylates e2) containing alkylene oxide groups comprise, in incorporated form, the following compounds: f, g and h; or f, h, i and m; or g and l; or i, l and m; or f, i, l and m; or f, h, k and m; and optionally other compounds, where f) is at least one diisocyanate,
g) is at least one compound of the formula IV

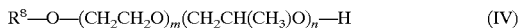

$$R^8\text{—}O\text{—}(CH_2CH_2O)_m(CH_2CH(CH_3)O)_n\text{—}H \quad (IV)$$

in which
the order of the alkylene oxide units is arbitrary,
$R^8$ is a straight-chain or branched $C_8$–$C_{30}$-alkyl radical, m and n independently of one another are an integer from 0 to 50, the sum m+n being at least 5, h) is at least one α,β-ethylenically unsaturated compound which, per molecule, additionally contains at least one group which is reactive toward isocyanate groups,
i) is a compound chosen from monohydric alcohols, diols, amines, diamines and aminoalcohols having at least one straight-chain or branched $C_8$–$C_{30}$-alkyl or -alkylene radical per molecule, and mixtures thereof,
k) is at least one aliphatic, cycloaliphatic or aromatic monoisocyanate,
l) is at least one α,β-ethylenically unsaturated compound which additionally contains at least one isocyanate group per molecule,
m) is at least one compound of the formula V

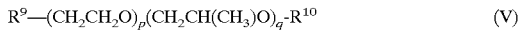

$$R^9\text{—}(CH_2CH_2O)_p(CH_2CH(CH_3)O)_q\text{-}R^{10} \quad (V)$$

in which
the order of the alkylene oxide units is arbitrary,
p and q are as defined above for m and n,
$R^9$ is OH or $NHR^{11}$, where $R^{11}$ is hydrogen, $C_1$–$C_8$-alkyl or $C_5$–$C_8$-cycloalkyl,
$R^{10}$ is H, $CH_2CH_2NHR^{11}$ or $CH_2CH(CH_3)NHR^{11}$.

According to one suitable embodiment, the urethane (meth)acrylates e2) additionally comprise, in incorporated form, at least one component chosen from n) compounds having a molecular weight in the range from 56 to 300 which contain two active hydrogen atoms per molecule,
o) polytetrahydrofurans having two active hydrogen atoms per molecule
p) polysiloxanes of the formula VI

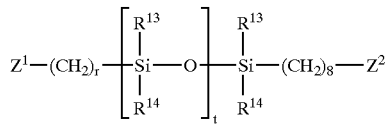

in which
$R^{13}$ and $R^{14}$ independently of one another are $C_1$–$C_4$-alkyl, benzyl, phenyl or a radical of the formula VII

$$\text{-}(CH_2)_U\text{—}O\text{—}(CH_2CH_2O)_v(CH_2CH(CH_3)O)_w\text{–}H \quad (VII)$$

in which
in formula VII the order of the alkylene oxide units is arbitrary,
U is an integer from 1 to 8,
v and w independently of one another are an integer from 0 to 200, the sum v+w being >0,
$Z^1$ and $Z^2$ independently of one another are OH, $NHR^{15}$ or a radical of the formula VII, where $R^{15}$ is hydrogen, $C_1$–$C_6$-alkyl or $C_5$–$C_8$-cycloalkyl, r and s independently of one another are from 2 to 8,
t is from 3 to 50,
and mixtures thereof.

Component f) is a customary aliphatic, cycloaliphatic and/or aromatic diisocyanate, such as tetramethylene diisocyanate, hexamethylene diisocyanate, methylenediphenyl diisocyanate, 2,4- and 2,6-toluylene diisocyanate and their isomeric mixtures, o- and m-xylylene diisocyanate, 1,5-naphthylene diisocyanate, 1,4-cyclohexylene diisocyanate, dicyclohexylmethane diisocyanate and mixtures thereof. Component f) is preferably hexamethylene diisocyanate, isophorone diisocyanate, o- and m-xylylene diisocyanate, dicyclohexylmethane diisocyanate and mixtures thereof. Where appropriate, up to 3 mol % of the specified compounds can be replaced by triisocyanates.

Component g) is preferably a compound of the formula IV in which the sum m+n is an integer from 5 to 70, preferably from 6 to 50.

$R^8$ in the formula IV is preferably n-octyl, ethylhexyl, 1,1,3,3-tetramethylbutyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, etc.

Suitable compounds g) are, for example, the abovementioned polyetherols suitable for the preparation of component e1), such as, for example, fatty alcohol alkoxylates.

Suitable monomers h) are the esters of α,β-ethylenically unsaturated mono- and dicarboxylic acids, such as acrylic acid, methacrylic acid, fumaric acid, maleic acid, itaconic acid, crotonic acid etc., with $C_1$–$C_{20}$-alkanediols. Examples thereof include 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc. Preference is given to using hydroxyethyl acrylate and hydroxyethyl methacrylate.

Suitable monomers h) are also the esters of the aboveinentioned acids with triols and polyols, such as, for example, glycerol, erythritol, pentaerythritol, sorbitol etc.

Suitable monomers h) are also the esters and amides of the abovementioned α,β-ethylenically unsaturated mono- and dicarboxylic acids with $C_2$–$C_{12}$-aminoalcohols which have a primary or secondary amino group. These include aminoalkyl acrylates and aminoalkyl methacrylates and their N-monoalkyl derivatives which carry, for example, an N—$C_1$–$C_8$-monoalkyl radical, such as aminomethyl acrylate, aminomethyl methacrylate, aminoethyl acrylate, aminoethyl methacrylate, N-methylaminomethyl acrylate, N-methylaminomethyl methacrylate, N-ethylaminomethyl acrylate, N-ethylaminomethyl methacrylate, N-(n-propyl) aminomethyl (meth)acrylate, N-isopropylaminomethyl (meth)acrylate and, preferably, tert-butylaminoethyl acrylate and tert-butylaminoethyl methacrylate. These also include N-(hydroxy-$C_1$–$C_{12}$-alkyl)(meth)acrylamides, such as N-hydroxymethyl(meth)acrylamide, N-hydroxyethyl(meth) acrylamide etc.

Suitable monomers h) are also the amides of the abovementioned α,β-ethylenically unsaturated mono- and dicarboxylic acids with di- and polyamines which have at least two primary or two secondary or one primary and one secondary amino group(s). Examples thereof include the corresponding amides of acrylic acid and methacrylic acid (designated below by the syllable "(meth)"), such as aminomethyl(meth)acrylamide, aminoethyl(meth) acrylamide, aminopropyl(meth)acrylamide, amino-n-butyl (meth)acrylamide, methylaminoethyl(meth)acrylamide, ethylaminoethyl(meth)acrylamide, methylaminopropyl (meth)acrylamide, ethylaminopropyl(meth)acrylamide, methylamino-n-butyl(meth)acrylamide etc.

Suitable monohydric alcohols i) have a straight-chain or branched alkyl radical having from 8 to 30 carbon atoms, which may optionally be additionally mono-, di- or poly-unsaturated. Suitable $C_8$–$C_{30}$-alkyl radicals are those given above. The alcohols i) can be used individually or as mixtures. Such alcohols and alcohol mixtures are, for example, obtainable by hydrogenation of fatty acids from natural fats and oils or from synthetic fatty acids, e.g. from the catalytic oxidation of paraffins. Suitable alcohols and alcohol mixtures i) are also obtainable by hydroformylation of olefins with simultaneous hydrogenation of the aldehydes, in which mixtures of straight-chain and branched primary alcohols (oxo alcohols) normally result. Suitable alcohols and alcohol mixtures i) are also obtainable by partial oxidation of n-paraffins by known processes, in which case largely linear secondary alcohols are obtained. Also suitable are the essentially primary, straight-chain and even-numbered Ziegler alcohols obtainable by organoaluminum synthesis.

Suitable monohydric alcohols i) are, for example, 1-, 2-, 3- and 4-octanol, 1-, 2-, 3-, 4- and 5-nonanol, 1-, 2-, 3-, 4- and 5-decanol, 1-, 2-, 3-, 4-, 5- and 6-undecanol, 1-, 2-, 3-, 4-, 5-, 6- and 7-dodecanol, 1-, 2-, 3-, 4-, 5-, 6-, 7- and 458-tridecanol, 1-, 2-, 3-, 4-, 5-, 6-, 7-, 8- and 9-tetradecanol, 1-, 2-, 3-, 4-, 5-, 6-, 7-, 8-, 9- and 10-pentadecanol, 1-, 2-, 3-, 4-, 5-, 6-, 7-, 8-, 9-, 10- and 11-hexadecanol, 1-, 2-, 3-, 4-, 5-, 6-, 7-, 8-, 9-, 10-, 11- and 12-heptadecanol, 1-, 2-, 3-, 4-, 5-, 6-, 7-, 8-, 9-, 10-, 11-, 12- and 13-octadecanol, etc. and mixtures thereof.

Suitable diols i) have at least one of the above-mentioned straight-chain or branched $C_8$–$C_{30}$-alkylene radicals. Examples thereof include 1,2-; 1,3-; 1,4-; 1,5-; 1,6-; 1,7- and 1,8-octanediol, 1,2- to 1,9-nonanediol, 1,2- to 1,10-decanediol, 1,2- to 1,11-undecanediol, 1,2- to 1,12-dodecanediol, 1,2- to 1,13-tridecanediol, 1,2- to 1,14-tetradecanediol, 1,2- to 1,15-pentadecanediol, 1,2- to 1,16-hexadecanediol, 1,2- to 1,17-heptadecanediol, 1,2- to 1,18-octadecanediol, etc. and mixtures thereof.

Suitable higher primary or secondary amines i) are amines and amine mixtures which have one or two of the above-mentioned $C_8$–$C_{30}$-alkyl radicals. These can, for example, be obtained by reaction of natural or synthetic fatty acids or fatty acid mixtures with ammonia to give nitrites, and subsequent hydrogenation. Examples thereof include alkylamines which have the alkyl radicals specified above for the monohydric alcohols i), i.e. the isomeric octyl-, nonyl-, decyl-, undecyl-, dodecyl-, tridecyl-, tetradecyl-, pentadecyl-, hexadecyl-, heptadecyl-, octadecylamines etc. and mixtures thereof.

Suitable diamines i) and aminoalcohols i) can have the alkylene radicals specified above for the diols i). These are then the isomeric octane-, nonane-, decane-, undecane-, dodecane-, tridecane-, tetradecane-, hexadecane-, heptadecane-, octadecanediamines and aminoalcohols etc. and mixtures thereof.

Suitable monoisocyanates k) are, for example, $C_8$–$C_{30}$-alkyl isocyanates, which are obtainable from the abovementioned amines and amine mixtures by phosgenation or from natural or synthetic fatty acids and fatty acid mixtures by Hofmann, Curtius or Lossen degradation.

Suitable cycloaliphatic monoisocyanates k) are, for example, cyclohexyl isocyanate, 2-, 3- and 4-methylcyclohexyl isocyanate, etc. and mixtures thereof.

Suitable aromatic monoisocyanates k) are, for example, phenyl isocyanate, 2-, 3- and 4-methylphenyl isocyanate, etc. and mixtures thereof.

Component 1) is, for example, an isocyanate of the formula VIII

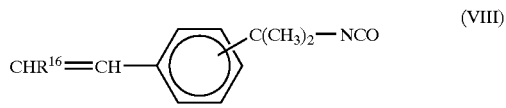

in which
the —C(CH$_3$)$_2$—NCO— groups can be in the o-, m- or p-position relative to the vinyl group, and $R^{16}$ is hydrogen or $C_1$–$C_8$-alkyl.

Preferably, in formula VIII, $R^{16}$ is hydrogen, methyl or ethyl.

The urethane (meth)acrylates e2) preferably contain, in incorporated form as component m), a compound of the formula V in which $R^9$ is OH or NHR$^{11}$, and $R^{10}$ is H, CH$_2$CH$_2$NHR$^{11}$ or CH$_2$CH(CH$_3$)NHR$^{11}$, where $R^{11}$ is hydrogen, methyl, ethyl, n-propyl, n-butyl, tert-butyl or cyclohexyl.

The preparation of these polyethers m), which have two groups which are reactive toward isocyanate groups, is carried out, for example, in the same way as the preparation of the polyetherols used in the polyether acrylates c) or e1). For this, the starter molecule water or a compound with two active hydrogen atoms, such as, for example, a diol or primary or secondary diamine, can be reacted with ethylene oxide and/or 1,2-propylene oxide individually, alternatingly one after the other or as a mixture. Compounds of formula V, which have at least one radical NHR$^{11}$ on the chain ends, can be prepared by amination of OH-terminated polyalkylene oxides with ammonia or primary amines. Suitable compounds of the formula V are, for example, the Cremophor®A products and Lutensol®AT products from BASF AG.

Component n) is preferably a diol, diamine, aminoalcohol, or mixture thereof. The molecular weight of these compounds is preferably in a range from about 56 to 280. Where appropriate, up to 3 mol % of the specified compounds can be replaced by triols or triamines.

Diols are preferably used as component n). Examples of diols which can be used are ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol.

Suitable aminoalcohols n) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc.

Suitable diamines n) are, for example, ethylenediamine, propylenediamine, 1,4-diaminobutane, 1,5-diaminopentane and 1,6-diaminohexane and α,ω-diamino polyethers, which can be prepared by amination of polyalkylene oxides with ammonia.

Component o) is preferably a polytetrahydrofuran with a number-average molecular weight in the range from about 300 to 5000, preferably from about 400 to 4000, in particular from 500 to 3000. Suitable polytetrahydrofurans o) can be prepared by cationic polymerization of tetrahydrofuran in the presence of acidic catalysts, such as, for example, sulfuric acid or fluorosulfuric acid. Such preparation processes are known to the person skilled in the art.

According to one suitable embodiment, the polysiloxanes p) of the formula VI do not have alkylene oxide radicals of the formula VII.

The polysiloxanes p) then preferably have a number-average molecular weight in the range from about 300 to 5000, preferably from 400 to 3000.

$R^{13}$ and $R^{14}$ are preferably then independently of one another $C_1$–$C_4$-alkyl, such as methyl, ethyl, n-propyl, isopropyl, n-butyl, sec-butyl or tert-butyl. Preferably $R^{13}$ and $R^{14}$ are both methyl.

$Z^1$ and $Z^2$ are preferably OH or $NH_2$.

According to another suitable embodiment, the polysiloxanes p) are silicone-poly(alkylene oxide) copolymers, where at least one or more of the radicals $Z_1$, $Z^2$, $R^{13}$ and/or $R^{14}$ are a radical of the formula VII.

Preferably, in formula VII, the sum v+w is chosen such that the molecular weight of the polysiloxanes p) is then in a range from about 300 to 30,000.

Preferably, the total number of alkylene oxide units in the polysiloxanes p), i.e. the sum v+w in the formula VII, is then in a range from about 3 to 200, preferably from 5 to 180.

The other radicals $R^{13}$ and/or $R^{14}$ are preferably chosen independently of one another from methyl, ethyl, n-propyl, isopropyl, n-butyl, sec-butyl, tert-butyl, pentyl, isopentyl, hexyl, octyl, 2-ethylhexyl, decyl, dodecyl und octadecyl, cyclohexyl, phenyl, naphthyl, benzyl, phenylethyl, tolyl, xylyl etc.

Preferably, at least one of the radicals $R^{13}$ or $R^{14}$ is methyl.

Suitable silicone-poly(alkylene oxide) copolymers p), which are known under the international nonproprietary name dimethicone, are the Tegopren® products from Goldschmidt, Belsil® 6031 from Wacker and Silvet® L from Witco.

According to a preferred embodiment, the preparation of the water-soluble or water-dispersible polymers used in the compositions according to the invention, urethane (meth)acrylates e2) containing alkylene oxide groups are used which comprise, in incorporated form,
  at least one diisocyanate f),
  at least one compound g), and
  at least one α,β-ethylenically unsaturated compound h), which additionally contains at least one active hydrogen atom per molecule.

In another preferred embodiment, these urethane (meth)acrylates then additionally comprise, in incorporated form, at least one component chosen from the abovementioned compounds n), o) and p) and mixtures thereof.

The urethane (meth)acrylates e2) containing alkylene oxide groups are prepared by reacting compounds chosen from components g), h), i), m) and mixtures thereof and optionally n), o), p) and mixtures thereof, which in each case contain, per molecule, at least one group which is reactive toward isocyanate groups, with at least one isocyanate-containing compound f), k) and/or 1). The components are chosen with the proviso that the urethane (meth)acrylates e2) comprise at least one αβ-ethylenically unsaturated double bond (components h and 1), at least 5 alkylene oxide units (components g and m) and at least one straight-chain or branched $C_8$–$C_{30}$-alkyl or -alkylene radical (components g, i and k) per molecule and at least one urethane or urea group (derived from components f, k and/or 1). Preferred urethane (meth)acrylates e2) comprise, in incorporated form, the compounds f, g and h; f, h, i and m; g and 1; i, 1 and m; f, 1, 1 and m; f, h, k and m and optionally other compounds chosen from the compounds of components f) to p) and mixtures thereof. Other suitable combinations are all those which satisfy the abovementioned proviso for the urethane (meth)acrylates e2).

The reaction temperature is generally in a range from about 60 to 140° C., preferably about 70 to 100° C. The reaction can be carried out without a solvent or in a suitable inert solvent or solvent mixture. Suitable solvents are aprotic polar solvents, e.g. tetrahydrofuran, ethyl acetate, n-methylpyrrolidone, dimethylformamide and, preferably, ketones, such as acetone and methyl ethyl ketone. The reaction is preferably carried out under an inert gas atmosphere, such as, for example, under nitrogen. The components are preferably used in amounts such that the ratio f) of NCO equivalent of the compounds of components f), k) and/or 1) to equivalent of active hydrogen atom of components g), h), i) and/or m) and, if present, n), o) and/or p) is in a range of from about 0.8:1 to 1.25:1, in particular from 1.05:1 to 1.15:1. If the resulting urethane (meth)acrylates c3) still have free isocyanate groups, the latter are then deactivated by the addition of alcohols, such as methanol, ethanol, etc., amines, aminoalcohols or mixtures thereof. Suitable aminoalcohols are described above as n), preferably 2-amino-2-methyl-1-propanol.

The urethane (meth)acrylates e2) preferably have a number-average molecular weight in the range of from about 400 to 8000, preferably from 500 to 6000.

The urethane (meth)acrylates e2) preferably have at least one, such as, for example, one, two or more, α,β-ethylenically unsaturated double bonds per molecule.

Preferably, the water-soluble or water-dispersible polymer used in the cosmetic compositions comprises, in copolymerized form,
  from 40 to 85% by weight, preferably from 45 to 80% by weight, of at least one component a),
  from 10 to 30% by weight, preferably from 15 to 25% by weight, of at least one component b),
  from 1 to 20% by weight, preferably from 2 to 15% by weight, of at least one component c),
  from 1 to 30% by weight, preferably from 2 to 25% by weight, of at least one component d),
where components c) and/or d) can be partially or completely replaced by a component e).

The water-soluble or water-dispersible polymers used in the cosmetic compositions according to the invention can comprise, in copolymerized form, up to 10% by weight, based on the total amount of the monomers to be polymerized, of at least one other free-radically polymerizable monomer. Examples thereof include esters of vinyl alcohol and allyl alcohol with $C_1$–$C_{40}$-monocarboxylic acids, vinyl ethers, vinyl aromatics, vinyl halides, vinylidene halides, $C_2$-$C_8$-monoolefins, nonaromatic hydrocarbons with at least 2 conjugated double bonds, N-vinylamides, N-vinyllactams, primary amides of $\alpha,\beta$-ethylenically unsaturated monocarboxylic acids, vinyl- and allyl-substituted heteroaromatic compounds and mixtures thereof.

According to one preferred embodiment, the polymer comprises:
from 40 to 85% by weight, preferably from 45 to 80% by weight, of at least one component a),
from 10 to 30% by weight, preferably from 15 to 28% by weight, of at least one component b),
from 1 to 20% by weight, preferably from 2 to 15% by weight, of at least one component c),
from 1 to 30% by weight, preferably from 2 to 25% by weight, of at least one component d).

In another preferred embodiment, the polymer comprises:
from 40 to 85% by weight, preferably from 45 to 80% by weight, of at least one component a),
from 10 to 30% by weight, preferably from 15 to 28% by weight, of at least one component b),
from 1 to 40% by weight, preferably from 5 to 35% by weight, in particular from 10 to 30% by weight, of at least one component e).

In another preferred embodiment, the polymer comprises:
from 40 to 85% by weight, preferably from 45 to 80% by weight, of at least one component a),
from 10 to 30% by weight, preferably from 15 to 28% by weight, of at least one component b),
from 0.1 to 20% by weight, preferably from 1 to 15% by weight, of at least one component c), as defined above,
from 1 to 40% by weight, preferably from 5 to 35% by weight, of at least one component e).

In another preferred embodiment, the polymer comprises:
from 40 to 85% by weight, preferably from 45 to 80% by weight, of at least one component a),
from 10 to 30% by weight, preferably from 15 to 28% by weight, of at least one component b),
from 0.1 to 30% by weight, preferably from 5 to 35% by weight, of at least one component d),
from 1 to 40% by weight, preferably from 5 to 35% by weight, of at least one component e).

The polymer used in the compositions according to the invention are prepared by free-radical polymerization by customary processes known to the person skilled in the art. These include free-radical bulk, emulsion, suspension and solution polymerization, preferably emulsion and solution polymerization. The amounts of compounds to be polymerized, based on solvents and dispersants, are generally chosen here such that about 30 to 80% by weight solutions, emulsions or dispersions are obtained. The polymerization temperature is generally from 30 to 120° C., preferably from 40 to 100° C. The polymerization medium for the solution polymerization can consist either of only one organic solvent or of a mixture of water and at least one water-miscible, organic solvent. Preferred organic solvents are, for example, alcohols, such as methanol, ethanol, n-propanol, isopropanol, n-butanol, ketones, such as acetone and methyl ethyl ketone, tetrahydrofuran etc. The solution polymerization can be carried out either as a batch process or in the form of a feed process, including monomer feed, staged and gradient procedures. Preference is generally given to the feed process, in which, if desired, some of the polymerization mixture is introduced as an initial charge and heated to the polymerization temperature, and then the remainder of the polymerization mixture, usually by way of one or more spatially separate feeds, is supplied to the polymerization zone continuously, in stages or under a concentration gradient, while the polymerization is maintained.

The initiators for the free-radical polymerization are customary peroxo or azo compounds. Examples thereof include dibenzoyl peroxide, tert-butyl perpivalate, tert-butyl per-2-ethylhexanoate, di-tert-butyl peroxide, 2,5-dimethyl-2,5-di(tert-butylperoxy)hexane, aliphatic or cycloaliphatic azo compounds, e.g. 2,2'-azobis(isobutyronitrile), 2,2'-azobis(2-methylbutyronitrile), 2,2'-azobis(2,4-dimethylvaleronitrile), 1,1'-azobis(1-cyclohexanecarbonitrile), 2-(carbamoylazo) isobutyronitrile, 4,4'-azobis(4-cyanovaleric acid) and the alkali metal and ammonium salts thereof, e.g. the sodium salt, dimethyl 2,2'-azobisisobutyrate, 2,2'-azobis[2-(2-imidazolin-2-yl)propane], 2,21-azobis(2-amidinopropane) and the acid addition salts of the latter two compounds, e.g., the dihydrochlorides.

Also suitable as initiators are hydrogen peroxide, hydroperoxides in combination with reducing agents, and persalts. Suitable hydroperoxides are, for example, t-butyl hydroperoxide, t-amyl hydroperoxide, cumene hydroperoxide and pinane hydroperoxide, in each case in combination with, for example, a salt of hydroxymethanesulfinic acid, an iron(II) salt or ascorbic acid. Suitable persalts are, in particular, alkali metal peroxodisulfates.

The amount of initiator used, based on the monomers, is generally in a range of from about 0.1 to 2% by weight, based on the total weight of the monomers to be polymerized.

The K values of the resulting copolymers are preferably in a range of from about 15 to 90, preferably from 20 to 70, in particular from 25 to 50 (1% strength by weight solution in ethanol). To achieve the desired K value it is possible, particularly in the case of emulsion or suspension polymerization, to use a regulator. Suitable regulators are, for example, aldehydes, such as formaldehyde, acetaldehyde, propionaldehyde, n-butyraldehyde and isobutyraldehyde, formic acid, ammonium formate, hydroxylammonium sulfate and hydroxylammonium phosphate. It is also possible to use regulators which contain sulfur in organically bonded form, such as di-n-butyl sulfide, di-n-octyl sulfide, diphenyl sulfide etc., or regulators which contain sulfur in the form of SH groups, such as n-butyl mercaptan, n-hexyl mercaptan or n-dodecyl mercaptan. Also suitable are water-soluble, sulfur-containing polymerization regulators, such as, for example, hydrogen sulfites and disulfites. Further suitable regulators are allyl compounds, such as allyl alcohol or allyl bromide, benzyl compounds, such as benzyl chloride or alkyl halides, such as chloroform or tetrachloromethane.

If desired, following the polymerization reaction, one or more polymerization initiators are added to the polymer solution, and the polymer solution is heated, for example to the polymerization temperature or to temperatures above the polymerization temperature in order to complete the polymerization. Suitable initiators are the azo initiators mentioned above, and also all other customary initiators suitable for free-radical polymerization in aqueous solution, for example peroxides, hydroperoxides, peroxodisulfates, percarbonates, peroxo esters and hydrogen peroxide. These take the polymerization reaction to a higher conversion, such as, for example, 99.9%. The solutions forming in the polymerization can, where appropriate, be converted into solid powders by a prior art drying technique. Preferred techniques are, for example, spray drying, spray fluidized-bed drying, roller drying and belt drying. Freeze drying and freeze concentration can likewise be used. If desired, the solvent can also be removed, partially or completely, by customary methods, e.g. distillation under reduced pressure.

The water-soluble or water-dispersible polymers used in the compositions according to the invention are anionic or anionogenic polymers. The acid groups of the polymers can be partially or completely neutralized with a base. Generally, the resulting salts of the polymers have better solubility or dispersibility in water than the nonneutralized polymers. Bases which can be used for neutralization of the polymers are alkali metal bases such as sodium hydroxide solution, potassium hydroxide solution, sodium carbonate, sodium hydrogencarbonate, potassium carbonate or potassium hydrogencarbonate, and alkaline earth metal bases such as calcium hydroxide, calcium oxide, magnesium hydroxide or magnesium carbonate, and ammonia and amines. Examples of suitable amines are $C_1$–$C_6$-alkylamines, preferably n-propylamine and n-butylamine, dialkylamines, preferably diethylpropylamine and dipropylmethylamine, trialkylamines, preferably triethylamine and triisopropylamine, $C_1$–$C_6$-alkyldiethanolamines, preferably methyl- or ethyldiethanolamine and di-$C_1$–$C_6$-alkylethanolamines. Particularly for use in hair-treatment compositions, 2-amino-2-methyl-1-propanol, 2-amino-2-ethylpropane-1,3-diol, diethylaminopropylamine and triisopropanolamine have proven successful for the neutralization of the polymers containing acid groups. The neutralization of the polymers containing acid groups can also be carried out using mixtures of two or more bases, e.g. mixtures of sodium hydroxide solution and triisopropanolamine. Depending on the intended use, the neutralization can be carried out partially, e.g. to from 5 to 95%, preferably from 30 to 95%, or completely, i.e. to 100%.

The polymers used in the compositions according to the invention have K values (measured in accordance with E. Fikentscher, Cellulose-Chemie 13 (1932), page 58–64, using a 1% strength by weight solution in ethanol) in a range of from about 15 to 90, preferably from 20 to 60. Their glass transition temperature is generally at least 0° C., preferably at least 20° C., particularly preferably at least 25° C. The glass transition temperature is then typically in a range of from about 30 to 130° C., in particular from to 100° C.

The polymers present in the compositions according to the invention can be used as auxiliaries in cosmetics and pharmacy, especially as or in coating compositions for keratinous surfaces (hair, skin and nails) and as coating compositions and/or binders for solid drug forms. In addition, they can be used as or in coating compositions for the textile, paper, printing, leather and adhesives industries. They are particularly suitable for use in hair cosmetics. The abovementioned polymers can also be used in creams and as tablet coatings and tablet binders. They are also suitable as binders and adhesives for cosmetic products, e.g. in the preparation of make-up, such as mascara and blusher, and in the preparation of cosmetic stick products, such as deodorant sticks, make-up sticks, etc.

The cosmetic compositions according to the invention are particularly suitable as coating compositions for keratinous surfaces (hair, skin and nails). The compounds used therein are water-soluble or water-dispersible. If the compounds used in the compositions according to the invention are water-dispersible, they can be used in the form of aqueous microdispersions having particle diameters of, customarily, from 1 to 250 nm, preferably from 1 to 200 nm. The solids contents in the preparations are here usually in a range of from about 0.2 to 20% by weight, preferably from 0.5 to 12% by weight. These microdispersions do not normally require emulsifiers or surfactants for stabilization.

The compositions according to the invention can preferably be in the form of a hair-treatment composition, especially in the form of a hair spray. For use as hair-setting agents, preferred compositions are those comprising polymers having at least a glass transition temperature $T_g$ of $\geq 20°$ C., preferably $\geq 30°$ C. The K value of these polymers is preferably in a range from 23 to 90, in particular from 25 to 60.

The compositions according to the invention generally comprise the polyurethanes in an amount in the range of from 0.2 to 20% by weight, based on the total weight of the composition.

The compositions are preferably hair-treatment compositions. They are usually in the form of an aqueous dispersion or in the form of an alcoholic or aqueous-alcoholic solution. Examples of suitable alcohols are ethanol, propanol, isopropanol etc.

In addition, the hair-treatment compositions according to the invention generally comprise customary cosmetic auxiliaries, for example softening agents, such as glycerol and glycol; emollients; perfumes; UV absorbers; dyes; antistatics; agents for improving combability; preservatives; and antifoams.

When formulated as hair sprays, the compositions according to the invention comprise a sufficient amount of a propellant. Preferred propellants are hydrocarbons (LPGs), in particular propane, n-butane, n-pentane and mixtures thereof. Suitable low-boiling propellants are also ethers, preferably dimethyl ether. If desired, compressed gases, such as nitrogen, air or carbon dioxide can also be used as propellant. The above-mentioned polymers used in the compositions according to the invention have good propellant compatibility, in particular good compatibility toward hydrocarbons, and can be formulated to give products with a high propellant content of, for example, at least 40% by weight, preferably at least 50% by weight, based on the total weight of the composition. Generally, however, it is also possible to keep the propellant content low in order to formulate products with a low VOC content. In such products, the propellant content is then generally no more than 55% by weight, based on the total weight of the composition. The hair-setting compositions according to the invention are also suitable for pump spray preparations without the addition of propellants.

The above-described polymers can also be used in combination with other hair polymers in the composition. Such polymers are, in particular:

nonionic, water-soluble or water-dispersible polymers or oligomers, such as polyvinylcaprolactam, e.g. Luviskol Plus (BASF), or polyvinylpyrrolidone a nd copolymers thereof, in particular with vinyl esters, such as vinyl acetate, e.g. Luviskol VA 37 (BASF); polyamides, e.g. those based on itaconic acid and aliphatic diamines;

amphoteric or zwitterionic polymers, such as the octylacrylamide/methyl methacrylate/tert-butylaminoethyl methacrylate/2-hydroxypropyl methacrylate copolymers obtainable under the names Amphomer® (Delft National), as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and their alkali metal and ammonium salts are preferred zwitterionic polymers. Other suitable zwitterionic polymers are methacroylethyl betaine/methacrylate copolymers, which are obtainable commercially under the name Amersette® (AMERCHOL) and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are available commercially, for example, under the names Resyn® (NATIONAL STARCH), Luviset® (BASF) and Gafset® (GAF), vinylpyrrolidone/vinyl acrylate copolymers, obtainable, for example, under the trade name Luviflex® (BASF). A preferred polymer is the vinylpyrrolidone/acrylate terpolymer obtainable under the name Luviflex® VBM-35 (BASF), acrylic acid/ethyl acrylate/N-tert-butylacrylamide terpolymers, which are marketed, for example, under the name Ultrahold® strong (BASF), and Luvimer® (BASF, terpolymer of t-butyl acrylate, ethylacrylate and methacrylic acid), or nonionic, siloxane-containing, water-soluble or -dispersible polymers, e.g. polyether siloxanes, such as Tegopren® (Goldschmidt) or Belsil® (Wacker).

The polymers according to the invention can be used with uncrosslinked and crosslinked siloxane-containing polyurethanes and/or with at least one other siloxane-free amide-containing hair polymer. Such polymers include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultrahold®(strong from BASF AG), the cationic polyurethanes described in DE-A-42 41 118, the above-described amide-containing amphoteric polymers (e.g. Amphomer®) and, in particular, copolymers which have a content of amide-containing monomers, such as N-vinyllactams, of at least 30% by weight, (e.g. Luviskol®plus and Luviskol®VA37 from BASF AG).

The other hair polymers are preferably present in amounts of up to 10% by weight, based on the total weight of the composition.

A preferred hair-treatment composition comprises:

i) from 0.5 to 20% by weight of at least one water-soluble or -dispersible polymer based on monomers of the formula I, as described above, ii) from 30 to 99.5% by weight, preferably from 40 to 99% by weight or from 40 to 98% by weight, of a solvent chosen from water and water-miscible solvents, preferably $C_2$–$C_5$-alcohols, in particular ethanol, and mixtures thereof, iii) from 0 to 70% by weight of a propellant, preferably one based on propane, n-butane and/or n-pentane or based on dimethyl ether, iv) from 0 to 10% by weight of at least one water-soluble or -dispersible hair polymer which is different from i), v) from 0 to 0.3% by weight of at least one water-insoluble silicone, vi) from 0 to 1% by weight of at least one nonionic, siloxane-containing, water-soluble or dispersible polymer, and customary additives.

The composition according to the invention can comprise, as component iv), at least one water-soluble or -dispersible hair polymer. The content of this component is then generally from about 0.1 to 15% by weight, preferably from 0.1 to 10% by weight, based on the total weight of the composition. Here, it is preferably to use water-soluble or water-dispersible polyurethanes which, if desired, additionally comprise siloxane groups in copolymerized form.

The composition according to the invention can comprise, as component v), at least one water-insoluble silicone, in particular a polydimethylsiloxane, e.g. the Abil® products from Goldschmidt. The content of this component is then generally from about 0.0001 to 0.2% by weight, preferably from 0.001 to 0.1% by weight, based on the total weight of the composition.

The composition according to the invention can comprise, as component vi), at least one nonionic, siloxane-containing, water-soluble or -dispersible polymer, in particular chosen from the above-described polyether siloxanes. The content of this component is then generally from about 0.001 to 2% by weight, based on the total weight of the composition The composition according to the invention can, where appropriate, additionally comprise an antifoam, e.g. one based on silicone. The amount of antifoam is generally up to 0.001% by weight, based on the total amount of the composition.

The compositions according to the invention have the advantage that, on the one hand, they impart the desired hold to the hair and, on the other hand, the polymers are easy to wash out (redispersible). Generally, a natural appearance and shine is imparted to the hair, even when the hair is by its very nature especially thick and/or dark.

In particular, the compositions according to the invention can be formulated to give hair-treatment compositions, in particular hairsprays, with a high propellant content. Advantageously, the hair-treatment compositions according to the invention essentially do not have a "flaking" effect.

The invention is illustrated in more detail by reference to the nonlimiting examples below.

EXAMPLES

Examples 1 to 3
Urethane (meth)acrylate preparation

An ethoxylated alcohol, in an amount in accordance with Table 1, in 100 g of acetone was introduced into a four-necked flask fitted with stirrer, dropping funnel, thermometer, reflux condenser and equipment for operating under nitrogen, and heated to about 60° C. Then, with stirring, isophorone diisocyanate was added dropwise in an amount in accordance with Table 1, and then the mixture was stirred under reflux for a further 60 min. In Examples 2 and 3 neopentyl glycol and hexamethylene diisocyanate were then added, likewise at about 60° C., directly one after the other to the mixture in an amount in accordance with Table 1. The reaction mixture was then stirred under reflux until the isocyanate group content of the mixture remained virtually constant, and then the mixture was cooled to room temperature with stirring. Where appropriate, a polysiloxanediamine ($M_n$=900 g/mol of Tegomer®A-Si 2122 from Goldschmidt, in the form of an 80% solution in acetone) (Example 3) was then added to the reaction mixture at a temperature of about 30° C. in an amount in accordance with Table 1. In all cases, tert-butylaminoethyl methacrylate was then added to the reaction mixture in an amount in accordance with Table 1 with stirring, the internal temperature not exceeding 40° C. After 300 g of ethanol had been added, the acetone was removed by distillation under reduced pressure at about 35° C., and then for further reaction, 50% strength by weight ethanolic solutions of the urethane (meth) acrylates were prepared by addition of further ethanol.

TABLE 1

| Ex. No. | Eth-oxy-late I[1] [mol] | Eth-oxy-late II[2] [mol] | NPG[3] [mol] | Poly-siloxane-diamine[4] [mol] | IPDI[5] [mol] | HDI[6] [mol] | tert-BAEMA[7] [mol] |
|---|---|---|---|---|---|---|---|
| 1 | 1 | — | — | — | 1 | — | 1 |
| 2 | — | 1 | 3 | — | 1 | 3 | 1 |
| 3 | — | 1 | 3 | 1 | 1 | 4 | 1 |

[1] $C_{16}$-, $C_{18}$-fatty alcohol ethoxylate, ca. 11 ethylene oxide units (Lutensol ® AT 11, BASF AG)
[2] $C_{16}$-, $C_{18}$-fatty alcohol ethoxylate, ca. 25 ethylene oxide units (Lutensol ® AT 25, BASF AG)
[3] NPG = neopentyl glycol
[4] polysiloxanediamine, $M_n$ = 900 g/mol (Tegomer ® A-Si 2122 from Goldschmidt)
[5] IPDI = isophorone diisocyanate
[6] HDI = hexamethylene diisocyanate
[7] tert-BAEMA = tert-butylaminoethyl methacrylate Comparative Examples C4 to C8, Examples 9 to 20:

I. Solution polymerization (Examples $C_4$–$C_8$, 9–20)

| Feed 1: | 244.8 g | of the monomer mixture in accordance with Table 2 |
|---|---|---|
| Feed 2: | 0.6 g | of 2,2'-azobis(2-methylbutyronitrile) |
|  | 120 g | of ethanol |
| Feed 3: | 2.0 g | of 2,2'-azobis(2-methylbutyronitrile) |
|  | 120 g | of ethanol |

A stirred apparatus fitted with reflux condenser and two separate feed devices was charged with 48 g of Feed 1 (monomer mixture in accordance with Table 2), 16.26 g of Feed 2 and 120 g of ethanol, and the mixture was heated to about 75° C. After partial polymerization, recognizable when the viscosity starts to increase, the remainder of Feed 1 was added over the course of 3 hours, and the remainder of Feed 2 was added over the course of 4 hours, the internal temperature being maintained at about 75–80° C. The mixture was then left to react at 80° C. for 4 hours. Feed 3 was then added over the course of half an hour, and the internal temperature increased to about 80° C. When the metered addition was complete, the mixture was afterpolymerized for a further 8 hours at this temperature.

II. Emulsion Polymerization (Examples C4, C5, 15,17)

The polymers from Examples C4, C5, 15 and 17 were also prepared by emulsion polymerization in accordance with the following procedure.

| Feed 1: | 300 g | of the monomer mixture in accordance with Table 2 |
|---|---|---|
|  | 100 g | of water |
|  | 1 g | of sodium lauryl sulfate |
|  | 6 g | of polyethoxysorbitan laurate (Tween ® 20, ICI) |
|  | 1.2 g | of ethylhexyl thioglycolate |
| Feed 2: | 0.9 g | of sodium persulfate |
|  | 100 g | of water |

460 g of water were heated to about 75° C. in a stirred apparatus fitted with reflux condenser and two separate feed devices. The preemulsified Feed 1 and Feed 2 were then added over the course of 2 hours, the temperature being maintained at about 75–80° C. If desired, the polymerization can be completed by adding an aqueous solution of a redox initiator (tert-butyl hydroperoxide), ascorbic acid) to the reaction mixture and afterpolymerizing.

TABLE 2

| Ex. No. | TBA[1] [% by wt.] | MAA[2] [% by wt.] | AA[3] [% by wt.] | EA[4] [% by wt.] | PEG-MA[5] [% by wt.] | SMA[6] [% by wt.] | UA-I[7] [% by wt.] | UA-II[8] [% by wt.] | UA-III[9] [% by wt.] | K value[10] |
|---|---|---|---|---|---|---|---|---|---|---|
| C4 | 70 | 23 | — | 7 | — | — | — | — | — | 39.7 |
| C5 | 70 | 23 | — | — | 7 | — | — | — | — | 42.4 |
| C6 | 70 | 23 | — | — | — | 7 | — | — | — | 41.3 |
| C7 | 67 | 23 | — | — | — | 10 | — | — | — | 42.1 |
| C8 | 72 | 21 | — | — | — | 7 | — | — | — | 43.8 |
| 9 | 66 | 22 | — | 5 | — | 7 | — | — | — | 42.2 |
| 10 | 62 | 22 | — | 7 | — | 9 | — | — | — | 45.7 |
| 11 | 62 | 22 | — | 7 | — | 9 | — | — | — | 38.9 |
| 12 | 58 | 23 | — | — | 7 | 10 | — | — | — | 42 |

TABLE 2-continued

| Ex. No. | TBA[1] [% by wt.] | MAA[2] [% by wt.] | AA[3] [% by wt.] | EA[4] [% by wt.] | PEG-MA[5] [% by wt.] | SMA[6] [% by wt.] | UA-I[7] [% by wt.] | UA-II[8] [% by wt.] | UA-III[9] [% by wt.] | K value[10] |
|---|---|---|---|---|---|---|---|---|---|---|
| 13 | 60 | 23 | — | — | 7 | 12 | — | — | — | 41.2 |
| 14 | 51 | 24 | — | — | 9 | 16 | — | — | — | 42.5 |
| 15 | 60 | 20 | — | — | — | — | 20 | — | — | 40.5 |
| 16 | 57 | 23 | — | — | — | 10 | — | 10 | — | 42.2 |
| 17 | 67 | 23 | — | — | — | — | — | — | 10 | 40.4 |
| 18 | 55 | 25 | — | — | — | 10 | — | — | 10 | 39.8 |
| 19 | 65 | — | 18 | — | 5 | 12 | — | — | — | 38.2 |
| 20 | 58 | — | 20 | — | 7 | 15 | — | — | — | 42.5 |

[1] TBA = tert-butyl acrylate
[2] MAA = methacrylic acid
[3] AA = acrylic acid
[4] EA = ethyl acrylate
[5] PEG-MA = polyethylene glycol methacrylate (Mw ≈ 350)
[6] SMA = stearyl methacrylate
[7]–[9] UA-I, -II, -III = urethane (meth)acrylates from Examples 1–3
[10] 1% strength by weight solution in ethanol Application examples Examples C21 to C23, 24 to 35

Aerosol hairspray formulations with a VOC content of 95% by weight:
Polyurethane according to Examples

| | |
|---|---|
| C6–C8, 9–20 | 5.00% by weight |
| Ethanol | 45.00% by weight |
| Propane/butane | 49.96% by weight |
| Perfume, additives | q.s. |

Examples C36 to C40, 41 to 52

Aerosol hairspray formulations with a VOC content of 80% by weight:
Polyurethane according to Examples

| | |
|---|---|
| C4–C8, 9–20 | 5.00% by weight |
| Ethanol | 40.00% by weight |
| Water | 15.00% by weight |
| Dimethyl ether | 39.96% by weight |
| Perfume, additives | q.s. |

Examples C53 to C57, 58–69

Aerosol hairspray formulations with a VOC content of 55% by weight:
Polyurethane according to Examples

| | |
|---|---|
| C4–C8, 9–20 | 5.00% by weight |
| Ethanol | 20.00% by weight |
| Water | 40.00% by weight |
| Propane/butane | 34.96% by weight |
| Perfume, additives | q.s. |

The curl retention of Examples C6 to C8 and 9 to 20 was measured for the abovementioned hairspray formulation having a VOC content of 95.

Curl retention=setting action on strands of hair in curl form at high atmospheric humidity (90%):

Curl retention is a measure of the hair-setting action. It is measured in a model test on locks of hair produced by a customary water-wave on hair about 15 cm long which has been sprayed with formulation A) for 4 seconds from a distance of 10 cm. After the suspended locks have spent 5 hours in a climatically controlled chamber (25° C., 90% relative atmospheric humidity), the relative deformation (extension) of the locks, based on their original shape, is determined. A high value denotes a high setting action, i.e. 100% corresponds to retention of the original shape of the suspended lock, 0% corresponds to a completely straightened hair. The results are given in Table 4.

Using the polymers from Comparative Examples $C_4$–$C_8$ and Examples 9–20 according to the invention, the n-heptane compatibility was determined as a measure of their propellant compatibility. For this, 1.5 g of each neutralized polymer and 23.5 g of ethanol were formulated to give 6% strength by weight solutions, which were titrated at room temperature with n-hexane until turbidity appeared. The results are also given in Table 4.

The polymers from Comparative Examples $C_4$–$C_8$ and from Examples according to the invention were formulated to give 5% strength by weight ethanolic solutions. They were applied to a glass plate, and the resulting films were tested with regard to 3 criteria, which are given in Table 3, and evaluated using grades 1–4. The ratings for the films are likewise given in Table 4.

TABLE 3

| | | Grade |
|---|---|---|
| A) Elasticity | hard and brittle | 4 |
| | hard | 3 |
| | average | 2 |
| | elastic | 1 |
| B) Tackiness | tacky | 4 |
| | slightly tacky (soft) | 3 |
| | slightly tacky (hard) | 2 |
| | not tacky | 1 |
| C) Smoothness | rough | 4 |
| | moderately smooth | 3 |
| | smooth | 2 |
| | very smooth | 1 |

TABLE 3-continued

| | | Grade |
|---|---|---|
| D) ability to be washed off | poor | 4 |
| | moderate | 3 |
| | good | 2 |
| | very good | 1 |

TABLE 4

| Polymer from Ex. No. | Curl retention [%] | n-Heptane compatibility [%] | A | B | C | D |
|---|---|---|---|---|---|---|
| C4 | 84 | 50 | 3–4 | 1 | 3 | 1–2 |
| C5 | 77 | 49 | 3*–4 | 2 | 2–3 | 1 |
| C6 | 87 | 60 | 3 | 1 | 2–3 | 3 |
| C7 | 88 | 3 | 1*–2 | 2–3 | 3–4 |
| C8 | 87 | 65 | 3–4 | 1 | 2–3 | 3–4 |
| 9 | 78 | 60 | 2–3 | 1 | 2 | 2 |
| 10 | 80 | 60 | 2 | 1 | 2 | 2–3 |
| 11 | 78 | 63 | 2 | 1*–2 | 2 | 2 |
| 12 | 80 | 62 | 2 | 1–2 | 1–2 | 1–2 |
| 13 | 82 | 64 | 2 | 1–2 | 1–2 | 1–2 |
| 14 | 79 | 67 | 2 | 1–2 | 1 | 1 |
| 15 | 75 | 55 | 1–2* | 1–2 | 2–3 | 1–2 |
| 16 | 80 | 63 | 2 | 1–2 | 1–2 | 1 |
| 17 | 82 | 60 | 2 | 1–2 | 1 | 1–2 |
| 18 | 76 | 66 | 1–2* | 1–2 | 1 | 1–2 |
| 19 | 78 | 62 | 2–3 | 2 | 2 | 2 |
| 20 | 81 | 61 | 2–3 | 2 | 2 | 1–2 |

*underlining indicates that the measured value is closer to the underlined value.

We claim:

1. A hair treatment composition comprising at least one water-soluble or water-dipersible polymer and a cosmetic auxiliary, wherein the polymer comprises, in copolymerized form, a) from 45 to 85% by weight of at least one $\alpha,\beta$-ethylenically unsaturated monomer of the formula I

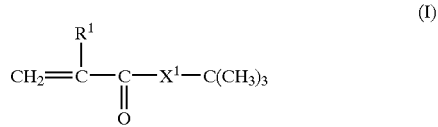

(I)

in which
 $R^1$ is hydrogen or $C_1$–$C_8$-alkyl, and
 $X^1$ is O or $NR^2$, where $R^2$ is hydrogen, $C_1$–$C_8$-alkyl or $C_5$–$C_8$-cycloalkyl, b) from 10 to 30% by weight of at least one $\alpha,\beta$-ethylenically unsaturated mono- and/or dicarboxylic acid, c) from 1 to 20% by weight of at least one compound having at leat one $\alpha,\beta$-ethylenically unsaturated double bond and at least 5 alkylene oxide units per molecule, chosen from polyether acrylates of the formula II

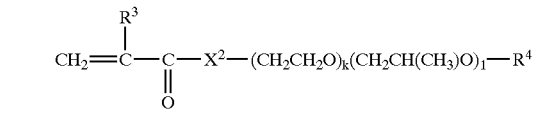

(II)

in which
 the order the alkylene oxide units is arbitrary,
 k and l independently of one another are an integer from 0 to 50, the sum of k+l being at least 5,
 $R^3$ is hydrogen or $C_1$–$C_8$-alkyl, and
 $R^4$ is hydrogen or $C_1$–$C_6$-alkyl,
 $X^2$ is O or $NR^2$, where $R^2$ is hydrogen, $C_1$–$C_8$-alkyl or $C_5$–$C_8$-cycloalkyl, d) from 1 to 30% by weight of at least one compound having at least one $\alpha,\beta$-ethylenically unsaturated double bond and at least one straight chain or branched $C_8$–$C_{30}$-alkyl or alkylene radical per molecule, chosen from compounds of the formula III

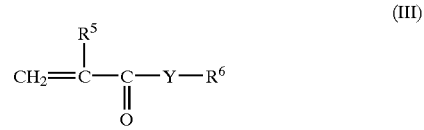

(III)

in which
 $R^5$ is hydrogen or $C_1$–$C_8$-alkyl,
 $R^6$ is a straight-chain or branched $C_8$–$C_{30}$-alkyl radical, and
 Y is O or $NR^7$, where $R^7$ is hydrogen, $C_1$–$C_8$-alkyl or $C_5$–$C_8$-cycloalkyl, where the components c) and/or d) can be partially or completely replaced by a component e), where e) is at least one compound having at least one ap-ethylenically unsaturated double bond, at least 5 alkylene oxide units and at least one straight-chain or branched $C_8$–$C_{30}$-alkyl or -alkylene radical per molecule, where component e) is chosen from e1) polyether acrylates of the formula II

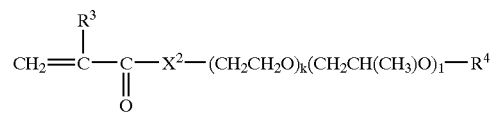

(II)

in which
 the order the alkylene oxide units is arbitrary,
 k and l independently of one another are an integer from 0 to 50, the sum of k+l being at least 5,
 $R^3$ is hydrogen or $C_1$–$C_8$-alkyl, and
 $R^4$ is $C_8$–$C_{30}$-alkyl,
 $X^2$ is O or $NR^2$, where $R^2$ is hydrogen, $C_1$–$C_8$-alkyl or $C_5$–$C_8$-cycloalkyl, e2) urethane (meth)acrylates containing alkylene oxide groups, and mixtures thereof, or salts thereof, and wherein the polymer is present in an effective amount to provide film-forming properties to the composition.

2. A composition as claimed in claim 1, where component e2) additionally comprises, in incorporated from, at least one component chosen from n) compounds having a molecular weight in the range from 56 to 300 which contain two active hydrogen atoms per molecule,
o) polytetrahydrofurans having two active hydrogen atoms per molecule
p) polysiloxanes of the formula VI

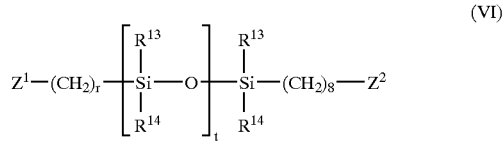

in which
$R^{13}$ and $R^{14}$ independently of one another are $C_1$–$C_4$-alkyl, benzyl, phenyl or a radical of the formula VII

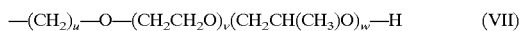

where in formula VII
the order of the alkylene oxide units is arbitrary,
u is an integer from 1 to 8,
v and w independently of one another are an integer from 0 to 200, the sum v+w being >0,
$Z^1$ and $Z^2$ independently of one another are OH, $NHR^{15}$ or a radical of formula VII, where $R^{15}$ is hydrogen, $C_1$–$C_6$-alkyl or $C_5$–$C_8$-cycloalkyl,
r and s independently of one another are from 2 to 8,
t is from 3 to 50,
and mixtures thereof.

3. A composition as claimed in claim 1, comprising a polymer which comprises, in copolymerized form,
   from 45 to 80% by weight, of at least one component a),
   from 15 to 28% by weight, of at least one component b),
   from 2 to 15% by weight, of at least one component c),
   from 2 to 25% by weight, of at least one component d),
where components c) and/or d) can be partially or completely replaced by a component e).

4. A composition as claimed in claim 1, comprising
   i) from 0.5 to 20% by weight of at least one water-soluble or -dispersible polymer, as defined in claim 1,
   ii) from 30 to 99.5% by weight, of at least one solvent chosen from water, water-miscible solvents and mixtures thereof,
   iii) from 0 to 70% by weight of a propellant,
   iv) from 0 to 10% by weight of at least one water-soluble or -dispersible hair polymer which is different from i),
   v) from 0 to 0.3% by weight of at least one water-insoluble silicone,
   vi) from 0 to 1% by weight of at least one nonionic, siloxane-containing, water-soluble or dispersible polymer.

5. A composition as claimed in claim 4, wherein component ii) is from 40 to 99% by weight.

6. A composition as claimed in claim 1, in the form of a hair spray.

7. The composition as claimed in claim 1, wherein the cosmetic auxiliaries are softening agents, emollients, perfumes, ultraviolet absorbers, dyes, antistatics, agents for improving combability, preservaties and antifoams.

8. The composition as claimed in claim 4, in the form of a hair spray.

9. The composition as claimed in claim 4, wherein the cosmetic auxiliaries are selected from softening agents, emollients, perfumes, ultraviolet absorbers, dyes, antistatics, agents for improving combability, preservaties and antifoams.

10. The composition as claimed in claim 4, wherein the water-soluble or -dispersible polymer (i) comprises, in copolymerized form,
    from 45 to 80% by weight, of at least one component a),
    from 15 to 28% by weight, of at least one component b),
    from 2 to 15% by weight, of at least one component c),
    from 2 to 25% by weight, of at least one component d),
and where components c) and/or d) can be partially or completely replaced by a component e).

* * * * *